(12) United States Patent
Yokhin

(10) Patent No.: US 6,535,575 B2
(45) Date of Patent: Mar. 18, 2003

(54) PULSED X-RAY REFLECTOMETER

(75) Inventor: Boris Yokhin, Nazareth Illit (IL)

(73) Assignee: Jordan Valley Applied Radiation Ltd., Migdal Haemek (IR)

( * ) Notice: Subject to any disclaimer, the term of this patent is extended or adjusted under 35 U.S.C. 154(b) by 0 days.

(21) Appl. No.: 10/077,125

(22) Filed: Feb. 14, 2002

(65) Prior Publication Data

US 2002/0150209 A1 Oct. 17, 2002

Related U.S. Application Data

(63) Continuation-in-part of application No. 09/833,902, filed on Apr. 12, 2001.

(51) Int. Cl.[7] .............................................. G01T 1/36
(52) U.S. Cl. ........................................... 378/82; 378/70
(58) Field of Search .................................... 378/82, 70

(56) References Cited

U.S. PATENT DOCUMENTS

| | | | |
|---|---|---|---|
| 5,574,284 A | 11/1996 | Farr | 250/370 |
| 5,619,548 A | 4/1997 | Koppel | 378/70 |
| 5,740,226 A | 4/1998 | Komiya et al. | 378/70 |
| 5,923,720 A | 7/1999 | Barton et al. | 378/84 |
| 6,389,102 B2 * | 5/2002 | Mayor et al. | 378/89 |

OTHER PUBLICATIONS

Chihab et al., "New Apparatus for Grazing X–Ray Reflectometry in the Angle–Resolved Dispersive Mode", Journal of Applied Crystallography 22 (1989), p. 460.

XTF5011 Tube, Produced by Oxford Instruments of Scotts Valley, California. Jun. 1999.

X –Ray Doubly–Bent Focusing Crystal Optic, Produced by XOS Inc., of Albany, New York. Jul. 2000.

Wiener et al., "Characterization of Titanium Nitride Layers by Grazing–Emission X–Ray Fluorenscence Spectrometry", in Applied Surface Science 125 (1998), p. 129.

Model S7032–0908N array, Produced by Hamamatsu, of Hamamatsu City, Japan. May 2000, Data sheet.

William Johnson et al., "ULSI Applications of Rapid X–Ray Reflectometry", Therma Wave, Inc. Jun. 26, 2000.

Jaklevic, et al., "High Rate X–Ray Fluorescence Analysis by Pulsed Excitation", IEEE Transactions on Nuclear Science NS–19:3 (1972), pp. 392–395.

Jaklevic, et al., "Small X–Ray Tubes for Energy Dispersive Analysis Using Semiconductor Spectrometers", Advances in X–Ray Analysis 15 (1972), pp. 266–275.

Jaklevic, et al., "Energy Dispersive X–Ray Fluorescence Spectrometry Using Pulsed X–Ray Excitation", Advances in X–Ray Analysis 19 (1976).

* cited by examiner

*Primary Examiner*—Craig E. Church
(74) *Attorney, Agent, or Firm*—Amster, Rothstein & Ebenstein

(57) ABSTRACT

Reflectometry apparatus includes a pulsed X-ray source, adapted to irradiate a sample with a sequence of pulses of radiation over a range of angles relative to a surface of the sample. An array of detector elements is positioned to receive the radiation reflected from the sample over the range of angles and to generate a signal indicative of respective charges accumulated by the detector elements due to photons of the radiation that are incident on the elements. Timing circuitry is coupled to the array so as to cause the charges to be cleared from the detector elements immediately before each of the pulses in the sequence, and to cause the signal from the elements to be sampled shortly after each of the pulses.

14 Claims, 10 Drawing Sheets

PULSED X-RAY REFLECTOMETER

CROSS-REFERENCE TO RELATED APPLICATION

This application is a continuation-in-part of U.S. patent application Ser. No. 09/833,902, filed Apr. 12, 2001, whose disclosure is incorporated herein by reference.

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Conventional X-ray reflectometers are sold by a number of companies, among them Technos (Osaka, Japan), Siemens (Munich, Germany) and Bede Scientific Instrument (Durham, UK). Such reflectometers typically operate by irradiating a sample with a beam of X-rays at grazing incidence, i.e., at a small angle relative to the surface of the sample, near the total external reflection angle of the sample material. Measurement of X-ray intensity reflected from the sample as a function of angle gives a pattern of interference fringes, which is analyzed to determine the properties of the film layers responsible for creating the fringe pattern. The X-ray intensity measurements are commonly made using a position-sensitive detector, such as a proportional counter or an array detector, typically a photodiode array or charge-coupled device (CCD).

A method for analyzing the X-ray data to determine film thickness is described, for example, in U.S. Pat. No. 5,740,226, to Komiya et al., whose disclosure is incorporated herein by reference. After measuring X-ray reflectance as a function of angle, an average reflectance curve is fitted to the fringe spectrum. The average curve is based on a formula that expresses attenuation, background and surface roughness of the film. The fitted average reflectance curve is then used in extracting the oscillatory component of the fringe spectrum. This component is Fourier transformed to find the film thickness.

U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. X-rays reflected or diffracted from the sample surface are received by a position-sensitive detector.

Various types of position-sensitive X-ray detectors are known in the art of reflectometry. Solid-state arrays typically comprise multiple detector elements, which are read out by a CCD or other scanning mechanism. Typically, each element accumulates photoelectric charge over a period of time before being read out and therefore cannot resolve the energy or number of incident X-ray photons. XRR systems known in the art that are based on such arrays simply record the total integrated radiation flux that is incident on each element. The signals at low angles, below the total external reflection angle, are usually much stronger than the signals above this angle. A ratio of $10^5$ to $10^7$ in photon flux between 0° and 3° reflections is typical. The dynamic range of array detection systems known in the art is substantially smaller than this ratio. Consequently, high-order fringes at higher incidence angles cannot generally be detected. Photon counting sensitivity is needed in order to measure the weak signals at these angles.

A further drawback of X-ray thin film measurement systems known in the art is their lack of spatial resolution. X-ray optics, such as the above-mentioned curved monochromators, are capable of focusing an X-ray beam to a spot diameter below 100 $\mu$m. When the beam is incident on a surface at a low angle, below 1°, for example, the spot on the surface is elongated by more than 50 times this diameter. A measurement that is made under these circumstances provides only an average of surface properties over the entire elongated area. For many applications, such as evaluating thin film microstructures on integrated circuit wafers, better spatial resolution is required.

Although the present patent application is concerned mainly with systems in which a sample is irradiated by a monochromatic beam, other methods for X-ray reflectometry are also known in the art. One such method is described, for example, in an article by Chihab et al., entitled "New Apparatus for Grazing X-ray Reflectometry in the Angle-Resolved Dispersive Mode," in *Journal of Applied Crystallography* 22 (1989), p. 460, which is incorporated herein by reference. A narrow beam of X-rays is directed toward the surface of a sample at grazing incidence, and a detector opposite the X-ray beam source collects reflected X-rays. A knife edge is placed close to the sample surface in order to cut off the primary X-ray beam, so that only reflected X-rays reach the detector. A monochromator between the sample and the detector (rather than between the source and sample, as in U.S. Pat. No. 5,619,548) selects the wavelength of the reflected X-ray beam that is to reach the detector.

SUMMARY OF THE INVENTION

It is an object of the present invention to provide improved methods and systems for X-ray analytical measurements, and particularly for measurements of thin film properties.

It is a further object of some aspects of the present invention to provide systems for X-ray reflectometry with enhanced dynamic range.

It is still a further object of some aspects of the present invention to provide systems for X-ray microanalysis with enhanced spatial resolution.

It is yet a further object of some aspects of the present invention to provide systems for measurement of X-ray reflectance with enhanced signal/noise ratio.

In preferred embodiments of the present invention, a system for X-ray reflectometry is used to determine properties of thin films on the surface of a sample, typically a semiconductor wafer. The sample is irradiated by a monochromatic beam of X-rays, which is focused to a small spot size on the surface of the sample. X-rays reflected from the surface are incident on a detector array, preferably a CCD array, each detector element in the array corresponding to a different angle of reflection from the surface. Charge stored by the detector elements is clocked out of the array to a processor, which analyzes the charges to derive a fringe pattern, corresponding to the intensity of X-ray reflection from the surface as a function of angle. The X-ray source, optics and processing circuitry in the system are arranged to achieve a high signal/noise ratio and high dynamic range, whereby high-order fringes are plainly apparent in the reflected signal. The processor analyzes the fringe pattern based on a physical model of thin film properties, including density, thickness and surface roughness. The high dynamic range enables the system to determine these properties accurately not only for the upper thin film layer, but also for one or more underlying layers on the surface of the sample.

In some preferred embodiments of the present invention, the sample is irradiated using a pulsed X-ray source, as is known in the art. The detector array is gated in synchronization with the pulsed source, preferably by clearing the charge stored by the array elements just before the source is fired, and then reading out the elements immediately after the excitation pulse. In this manner, the integrated contribution of steady-state background effects, such as thermal noise, to the output of the detector array is reduced in proportion to the gating duty cycle of the array. On the other hand, as long as the average power of the X-ray source is the same in pulsed mode as in conventional constant-wave (CW) operation, the same total signal output from the detector array is maintained. In this manner, a significant improvement is achieved in signal/noise ratio of the system.

Although preferred embodiments of the present invention are directly mainly toward enhancing X-ray reflectometric measurements on thin films, and particularly on semiconductor wafers, the principles of the present invention can similarly be used in other applications of X-ray reflectometry, as well as in other types of radiation-based analysis.

There is therefore provided, in accordance with a preferred embodiment of the present invention, reflectometry apparatus, including:

a pulsed X-ray source, adapted to irradiate a sample with a sequence of pulses of radiation over a range of angles relative to a surface of the sample;

an array of detector elements, positioned to receive the radiation reflected from the sample over the range of angles and to generate a signal indicative of respective charges accumulated by the detector elements due to photons of the radiation that are incident on the elements; and timing circuitry, coupled to the array so as to cause the charges to be cleared from the detector elements immediately before each of the pulses in the sequence, and to cause the signal from the elements to be sampled shortly after each of the pulses.

Typically, the sample includes one or more thin film layers, and the reflected radiation is characterized by an oscillatory variation of intensity as a function of the angles due to the thin film layers, and the array of detector elements is adapted to detect the oscillatory variation. Preferably, the apparatus includes a processor, which is coupled to receive the signal from the array of detector elements and to analyze the oscillatory variation to determine one or more properties of the one or more thin film layers. Most preferably, the processor is adapted to estimate, responsive to the respective charges, a number of the photons that was incident on each of the elements.

Further typically, the detector elements are characterized by a background current, which causes a noise charge to be accumulated by the detector elements irrespective of the radiation, and by causing the charges to be cleared from the detector elements, the timing circuitry is operative to reduce the noise charge in the signal sampled from the elements shortly after each of the pulses. In a preferred embodiment, the array of detector elements includes a charge coupled device (CCD).

Preferably, the timing circuitry is coupled to synchronize clearing of the charges from the detector elements and sampling of the signal therefrom with the pulses from the X-ray source.

There is also provided, in accordance with a preferred embodiment of the present invention, a method for reflectometry, including:

positioning an array of detector elements to receive radiation reflected from a sample and to generate, responsive to the radiation, a signal indicative of respective charges accumulated by the detector elements due to photons of the radiation that are incident on the elements;

irradiating a sample with a sequence of pulses of the radiation over a range of angles relative to a surface of the sample;

clearing the charges from the detector elements immediately before each of the pulses in the sequence; and sampling the signal from the elements shortly after each of the pulses so as to determine a pattern of the reflected radiation over the range of angles.

The present invention will be more fully understood from the following detailed description of the preferred embodiments thereof, taken together with the drawings in which:

DETAILED DESCRIPTION OF PREFERRED EMBODIMENTS

Figure 1:
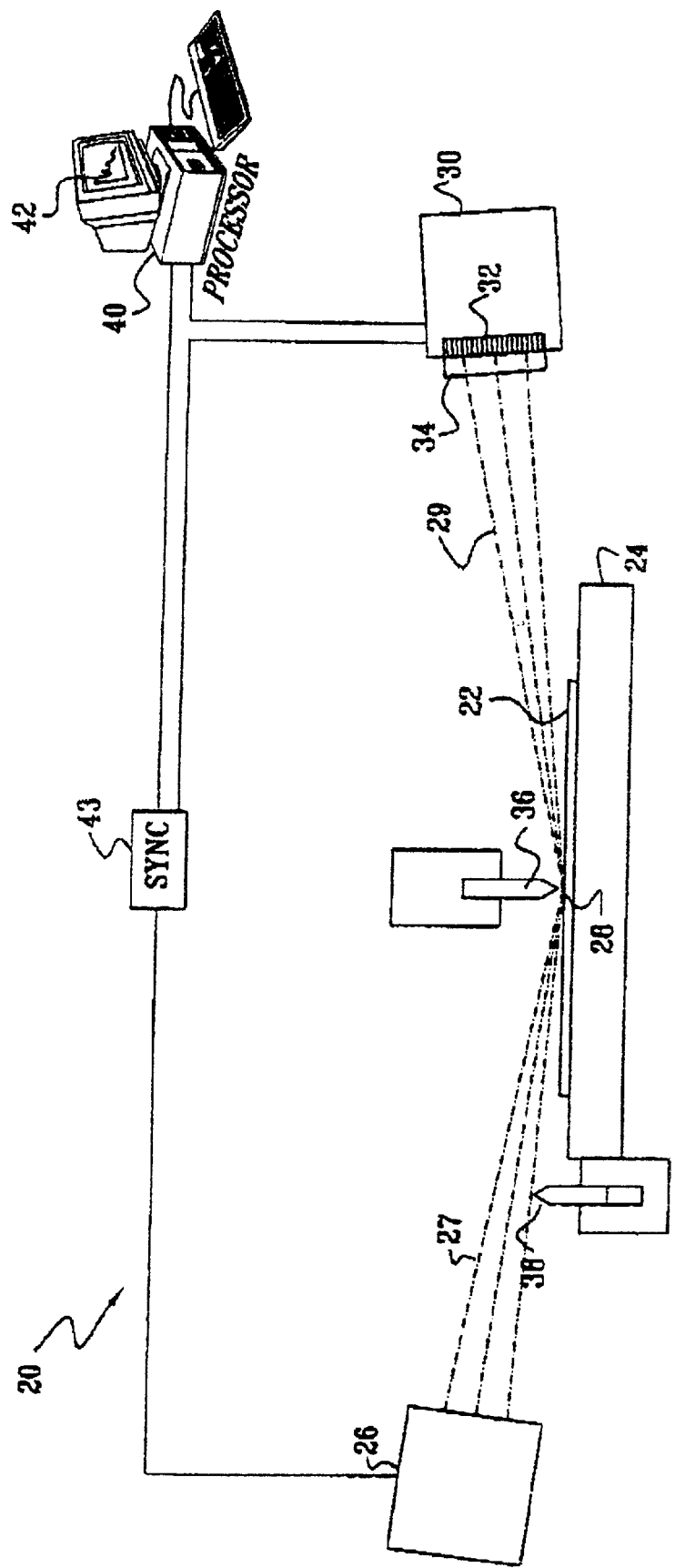
FIG. 1 is a schematic illustration of a system for X-ray reflectometry, in accordance with a preferred embodiment of the present invention.

FIG. 1 is a schematic illustration of a system 20 for X-ray reflectometry of a sample 22, in accordance with a preferred embodiment of the present invention. The sample is preferably mounted on a motion stage 24, allowing accurate adjustment of its position and orientation. An X-ray source 26, typically an X-ray tube with suitable monochromatizing optics (not shown), irradiates a small area 28 on sample 22. A preferred X-ray tube for this purpose is the XTF5011 tube, produced by Oxford Instruments of Scotts Valley, Calif. A number of different optical configurations that may be used in source 26 are described in U.S. patent application Ser. No. 09/408,894, which is assigned to the assignee of the present patent application and is incorporated herein by reference. The optics preferably comprise a curved crystal monochromator, such as the Doubly-Bent Focusing Crystal Optic, produced by XOS Inc., of Albany, N.Y. Other suitable optics are described in patent application Ser. No. 09/408,894 and in the above-mentioned U.S. Pat. Nos. 5,619,548 and 5,923,720. Further possible optical configurations will be apparent to those skilled in the art. A typical X-ray energy for reflectometric measurements in system 20 is about 8.05 keV (CuKal). Alternatively, other energies may be used, such as 5.4 keV (CrKal). A dynamic knife edge 36 and shutter 38 are preferably used to limit an incident beam 27 of the X-rays, as described further hereinbelow.

A reflected beam 29 of X-rays from sample 22 is collected by a detector assembly 30. Preferably, assembly 30 collects reflected X-rays over a range of reflection angles between about 0° and 3°, both below and above the critical angle of the sample for total external reflection. Assembly 30 comprises a detector array 32, preferably a CCD array, as described hereinbelow. Although for simplicity of illustration, only a single row of detectors elements is shown in FIG. 1, with a relatively small number of detector elements, in preferred embodiments of the present invention, array 32 generally includes a greater number of elements, arranged in either a linear or a matrix (two-dimensional) array. Assembly 30 further comprises a window 34 made of a suitable X-ray transparent material, such as beryllium, spaced in front of the detector array, between the array and the sample.

A reflectometry processor 40 analyzes the output of assembly 30, so as to determine a distribution 42 of the flux of X-ray photons reflected from sample 22 as a function of angle at a given energy or over a range of energies. Typically, sample 22 has one or more thin surface layers, such as thin films, at area 28, so that distribution 42 exhibits an oscillatory structure due to interference effects among reflected X-ray waves from the interfaces between the layers. The processor analyzes characteristics of the oscillatory structure in order to determine the thickness, density and surface quality of one or more of the surface layers, using methods of analysis described hereinbelow.

System 20 is also shown as including an optional synchronization controller 43, which is preferably under the command of processor 40. Controller 43 is used in an alternative embodiment of the present invention to synchronize pulsed operation of X-ray source 26 with gating of detector assembly 30. This embodiment is described further hereinbelow with reference to FIG. 10.

Although in the preferred embodiment shown in FIG. 1, system 20 is described with reference to X-ray reflectometry, it will be appreciated that the system may similarly be used, mutatis mutandis, in other fields of X-ray analysis. Possible fields of application include X-ray fluorescence (XRF) analysis, including particularly grazing emission XRF, as well as other XRF techniques known in the art. Grazing emission XRF is described, for example, in an article by Wiener et al., entitled "Characterization of Titanium Nitride Layers by Grazing-Emission X-ray Fluorescence Spectrometry," in *Applied Surface Science* 125 (1998), p. 129, which is incorporated herein by reference. Furthermore, the principles of system 20 may be implemented in position-sensitive detection systems for other energy ranges, such as for detection of gamma rays and other nuclear radiation.

Figure 2:
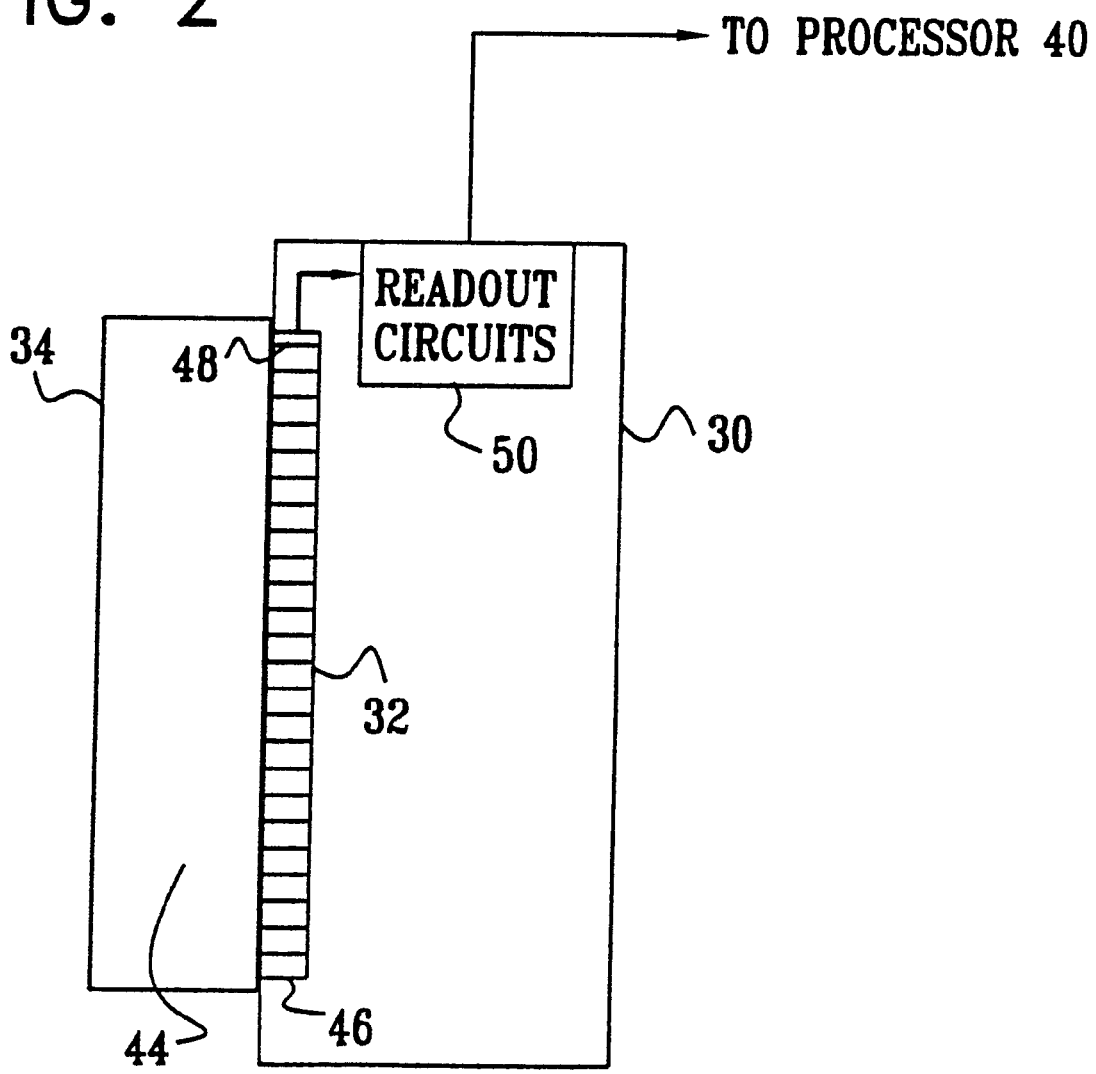
FIG. 2 is a schematic block diagram illustrating an X-ray detection assembly used in the system of FIG. 1, in accordance with a preferred embodiment of the present invention.

FIG. 2 is a block diagram that schematically shows details of detector assembly 30, in accordance with a preferred embodiment of the present invention. As noted above, detector array 32 preferably comprises a CCD array, such as the model S7032-0908N array produced by Hamamatsu, of Hamamatsu City, Japan. This array comprises 536×256 pixels, with an overall size of 12.6×6 mm, and is preferably operated in a line-binning mode, using special hardware supplied for this purpose by Hamamatsu. Alternatively, the detector array may comprise an array of PIN diodes with suitable readout circuits, possibly including integrated processing electronics, as described in U.S. patent application Ser. No. 09/409,046, which is assigned to the assignee of the present patent application and is incorporated herein by reference application Ser. No. 09/409,046 also describes alternative features of the array, including various geometrical configurations of the array (both one- and two-dimensional) and masking that may be applied to enhance the array's detection properties. These features are applicable to assembly 30 of the present patent application, as well. In any event, it will be understood that these detector types are described here by way of example, and detectors of any suitable type, dimension and number can be used.

Detector assembly 30 comprises an evacuable enclosure 44 adjacent to detector array 32. The front side of enclosure 44, between array 32 and sample 22, is closed off by window 34, and the enclosure is evacuated during operation. Preferably, the distance from array 32 to window 34 is at least equal to the length of the array, measured from a first detector element 46 to a last detector element 48, and is most preferably at least two to three times the length of the array. (First detector element 46 is positioned to capture the lowest-angle reflected photons, around 0°, while last element 48 captures the highest-angle photons, typically near 3°.) The inventors have found that removal of the air from the region immediately in front of the array, along with distancing the window from the array, substantially reduces the number of scattered X-ray photons that reach the array. When array 32 operates in air, or when window 34 is positioned close to the array, scatter of photons reflected from sample 22 at low angles ordinarily makes a substantial contribution to the signal background at high angles. Because the low-angle reflections are generally so intense by comparison with the high-angle reflections, this background significantly degrades or even masks the high-angle signal. The use of window 34 and evacuated enclosure 44, as shown in FIG. 2, eliminates most of this scatter background, without the difficulty and expenses of having to evacuate the entire system.

A further source of background in assembly 30 is residual charge in the CCD shift register of array 32. CCDs operate by transferring charge in a "bucket brigade" mode, from one element to the next down the array. The charge is thus transferred, one pixel at a time, to readout circuits 50, which are coupled to an output of the array at last element 48. Although CCDs are highly efficient in transferring charge from element to element, there is still a small amount of residual charge left behind in each transfer, which is roughly proportional to the amount of charge transferred. In the configuration shown in FIG. 2, after each X-ray exposure period, last element 48 is read out first, while first element 46 is read out last, after its charge has been transferred down the entire array. By positioning array 32 so that last element 48, which typically receives the weakest X-ray signal, is read out first, the background level due to residual charge in the weak signal elements near element 48 is minimized. The background added to the strong signals from detector elements near first element 46, due to reading these signals out last, is not significant by comparison with the strength of the signals themselves.

Figure 3:
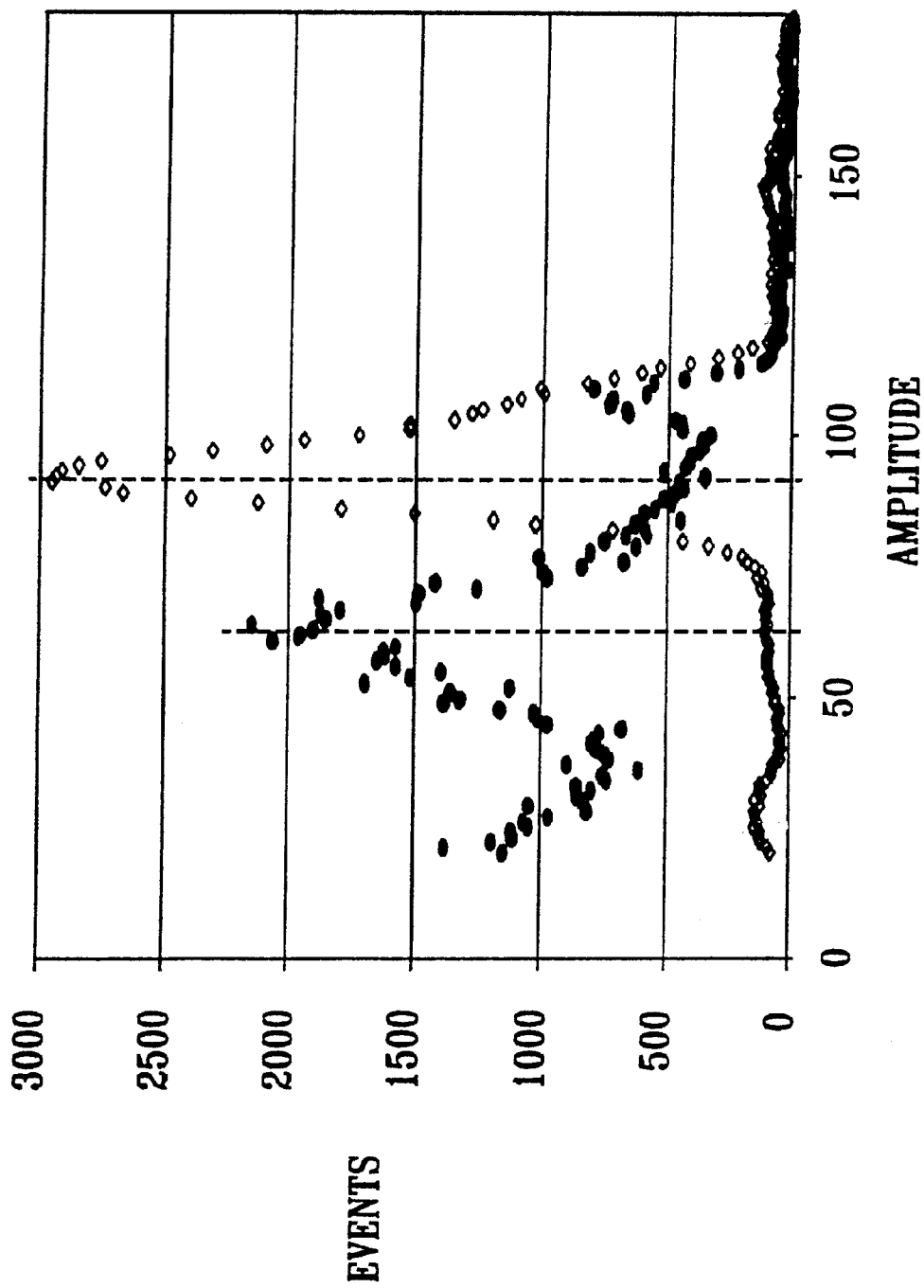
FIG. 3 is a schematic plot of charge amplitude collected by an detector on which X-ray photons of a given energy are incident, in accordance with a preferred embodiment of the present invention.

FIG. 3 is a schematic plot showing the response of the elements of detector array 32 to incident photons, in accordance with a preferred embodiment of the present invention. In this experiment, the detector array was irradiated with monochromatic X-ray radiation, and signals were gathered from the array in two different read-out modes. The amplitude units of the horizontal axis are arbitrary, but indicate the estimated number of electrons generated for each X-ray photon that is incident on an element of the array, based on the output signal from the array. Each incident photon constitutes an "event," and the vertical axis shows, for each value of the amplitude, how many times a charge of that amplitude was generated by an incident photon.

As can be seen in the figure, the distribution of events is substantially different for the different read-out modes. The charge generated due to an incident photon may typically be distributed between two adjacent pixels. The curve having a sharp peak near amplitude 100 is accordingly generated by combining the charge counted in adjacent pixels. This read-out mode, however, can be applied only when the flux is low enough so that during any given read-out frame, there is generally no more than one incident photon per pixel, with most pixels receiving no photons. At high flux, with many photons incident on each element, this "charge combining" approach cannot be used. In this case, the event distribution has the form of the second curve shown in FIG. 3, with a peak near amplitude 60. Such behavior was observed for both Cu Kα (8.05 keV) and Cr Kα (5.41 keV) irradiation. The inventors have empirically found that the combination of these two read-out modes for high- and low-flux conditions can be used effectively in converting the electrical signal levels received from array 32 into units of photon counts over a very large dynamic range, as is commonly encountered in XRR measurements.

Figure 4:
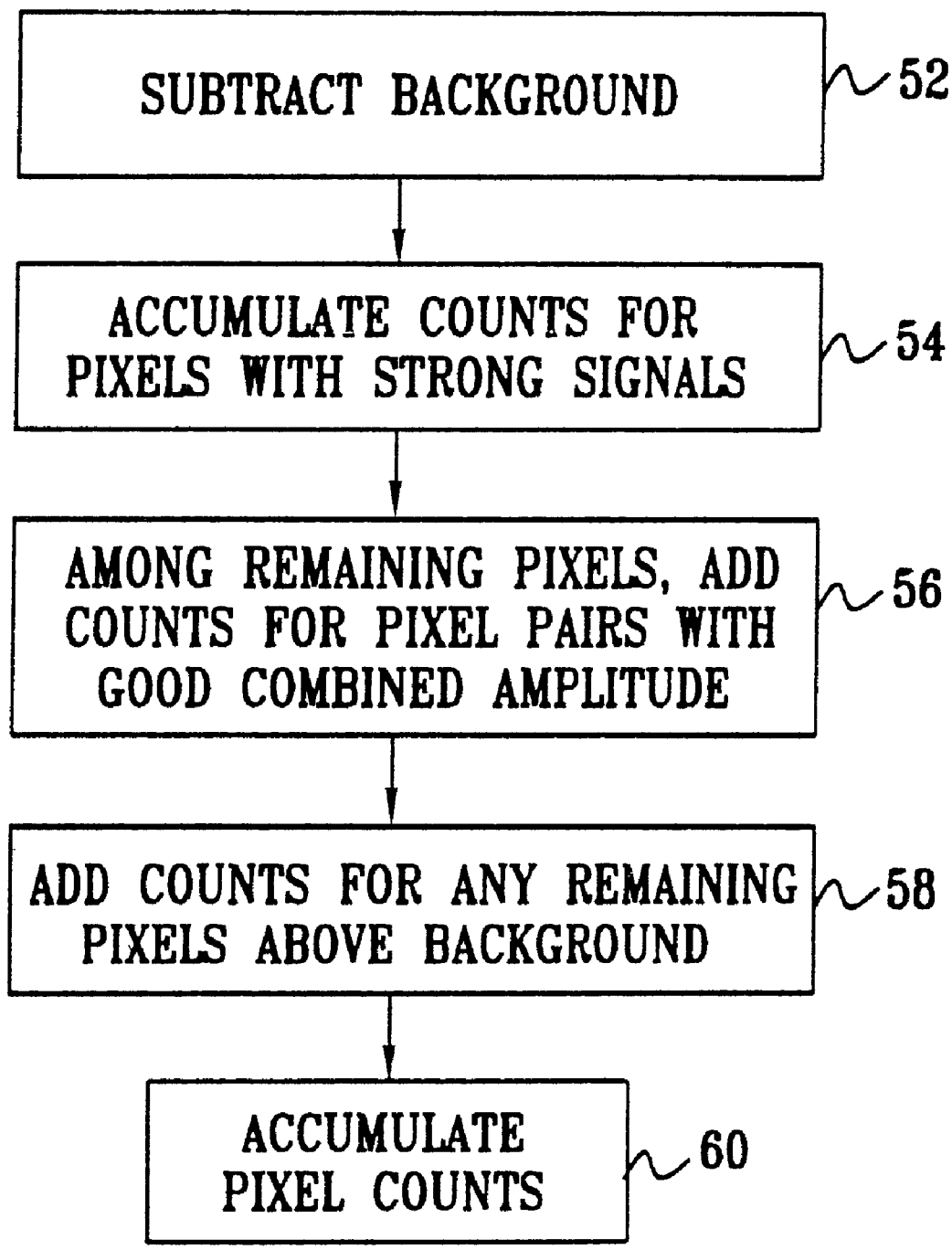
FIG. 4 is a flow chart that schematically illustrates a method for processing signals generated by an X-ray detector array, in accordance with a preferred embodiment of the present invention.

FIG. 4 is a flow chart that schematically illustrates a method for analyzing signals received by detector array 32, in accordance with a preferred embodiment of the present invention. The method is based on the principles described above with reference to FIG. 3. It is actuated by processor each time charge is read out of the elements of the array, with respect to each of the elements in turn, in order to translate the charge amplitude measured in each element into units of incident X-ray photons.

The method includes four operations, which are performed over all of the pixels in the array:

1. In a background subtraction step 52, a general background level is subtracted from the digitized signal level measured in each of the pixels, thus generating a background-subtracted level y(j) for each pixel. The general background level is found by measuring the dark current output of the detector array in the absence of incident radiation.

2. In a strong flux counting step 54, the signal levels after background subtraction are compared to a high signal threshold, which is determined based on the high-flux mode of the distribution shown in FIG. 3. Specifically, the processor finds pixels (i.e., detector array elements) whose signal levels, y(j), are greater than three times a signal amplitude parameter, Av1, which is determined empirically based on the location of the peak in the high-flux single-photon signal (such as the high-amplitude peak shown in FIG. 3). For each such pixel j, the number of photon counts n(j) for the pixel is determined to be n(j)=int{[y(j)−BL1]/Av1}, wherein BL1 is an empirical background threshold. Processor 40 then sets the signal level for the pixel to zero, so that it is not counted again in subsequent steps.

3. In a pixel pair counting step 56, the processor searches the remaining pixels, not counted in step 54, to find pairs of adjacent pixels whose total signal level (summed over the pair) is roughly equal to a low-flux single-photon signal amplitude parameter Av2. This parameter, as well as a second background threshold BL2, is determined empirically. Specifically, the inventors have found that setting Av2=Av1 gives good results. BL1 and BL2 are set so that the high- and low-intensity portions of the photon energy spectrum, found at steps 54 and 56 respectively, will match up. Based on these parameters, at step 56, the processor finds pairs of pixels that satisfy |y(j)+y(j+1)−Av2|<BL2. For each such pair, the processor records a single photon count, which is arbitrarily assigned to the photon count n(j) for the first of the two pixels. The signal levels in these pixels are then zeroed, as well.

4. In a remainder counting step 58, any other pixels with significant signal levels that were not counted at step 54 or 56 are evaluated. To carry out this step, any pixel signal values y(j) that are below the background level, so that y(j)<0 after background subtraction at step 52, are set to y(j)=0. Then, for each pixel that is a local maximum (i.e., greater signal value y(j) than its immediate neighbors), the pixel photon count n(j) receives the value n(j)=int{[y(j)+y(k)−BL1]/Av1}, wherein y(k) is the higher of the signal levels of the two pixels, j+1 and j−1, neighboring on pixel j. The values y(j) and y(k) are then set to zero. For any remaining pixels (not local maximum or their higher neighbors), the photon count receives the value n(j)=int{[y(j)−BL1]/Av1}, and y(j) is zeroed.

After all four of the steps listed above are completed, the array is reset, and the processor is ready to receive the next signal readout from array 32. The number of counts determined for each of the pixels is accumulated in a respective register, in a count accumulation step 60. The steps of signal readout and processing, as described above, are preferably repeated enough times to determine a count spectrum over the entire array. Using this technique, fringe structure can be seen not only at the low-angle, high-flux pixels, where many pixels are incident in each signal readout cycle, but also at high angles, where only one count or less may arrive at each pixel in a given cycle.

Figure 5A:
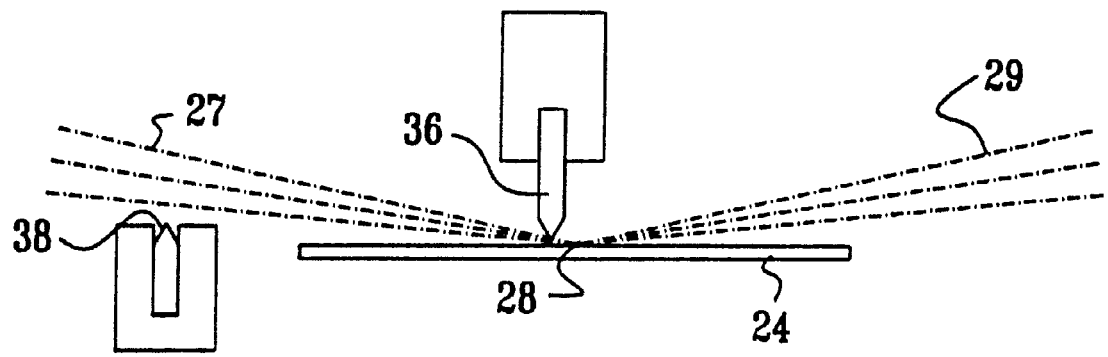
FIGS. 5A and 5B are schematic detail views of the system of FIG. 1, illustrating the operation of a dynamic knife edge and shutter used in the system, in accordance with a preferred embodiment of the present invention.
Figure 5B:
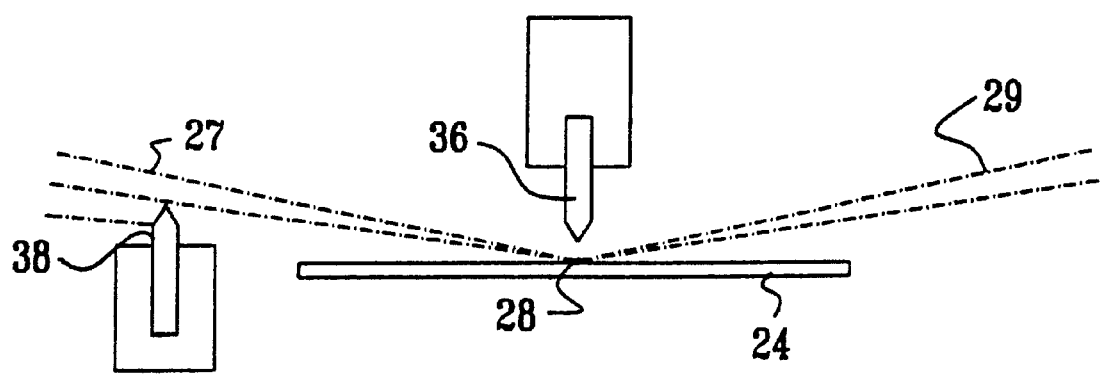

FIGS. 5A and 5B are detail views of system 20, illustrating the use of knife edge 36 and shutter 38, in accordance with a preferred embodiment of the present invention. In FIG. 5A, the knife edge and shutter are positioned to allow optimal detection of low-angle reflections, near 0°. Shutter 38 is withdrawn outside the extent of incident beam 27. Knife edge 36 is positioned to cut the upper portion of the incident beam. As a result, most of the incident beam is cut off, and the lateral dimension of the X-ray spot incident on area 28 is reduced. Preferably, the knife edge is lowered to within less than 10 µm of the surface of sample 22, and most preferably to as little as 1 µm from the surface. The lateral dimension of the spot is thus reduced to 1 mm or less, instead of the typical dimension of 5 mm or more when the knife-edge is not used. The reduced spot size on the sample means that low-angle reflection measurements made by system 20 have enhanced spatial resolution, providing more detailed information about thin film microstructures on sample 22. Alternatively or additionally, when a certain area of the sample, such as a patterned semiconductor wafer, must be set aside for testing, the small spot size enables a smaller portion of sample "real estate" to be used for this purpose.

Moreover, the inventors have found that wafers are prone to warping, particularly when held by a vacuum chuck, as is commonly practiced in test and fabrication equipment. When the X-ray spot is spread over a long lateral dimension, this warping can cause different parts of the spot to be incident on the wafer at slightly different angles. As a result, the fringe structure in the measured distribution of the reflected radiation is blurred. Thus, an additional benefit of the use of knife edge 36 is the reduction of this blurring due to warping of the wafer, since the range of angles of incidence of the X-rays within the spot is accordingly narrowed.

In FIG. 5B, knife edge 36 and shutter 38 are positioned to enable effective detection of weaker, high-angle reflection. In this case, the knife edge is withdrawn from the beam, while the shutter is positioned to cut off the low-angle portion of incident beam 27. Alternatively, the shutter may be positioned to cut off the low-angle portion of reflected beam 29. Only the high-angle reflections from sample 22 reach the detector array, and not the strong low-angle reflections. As a result, the background level at the high-angle elements of the detector array is reduced, and X-ray photons can be collected by the array over a substantially longer integration period without saturation. Thus, the weak, high-angle signals are detected with enhanced signal/noise ratio.

Figure 6:
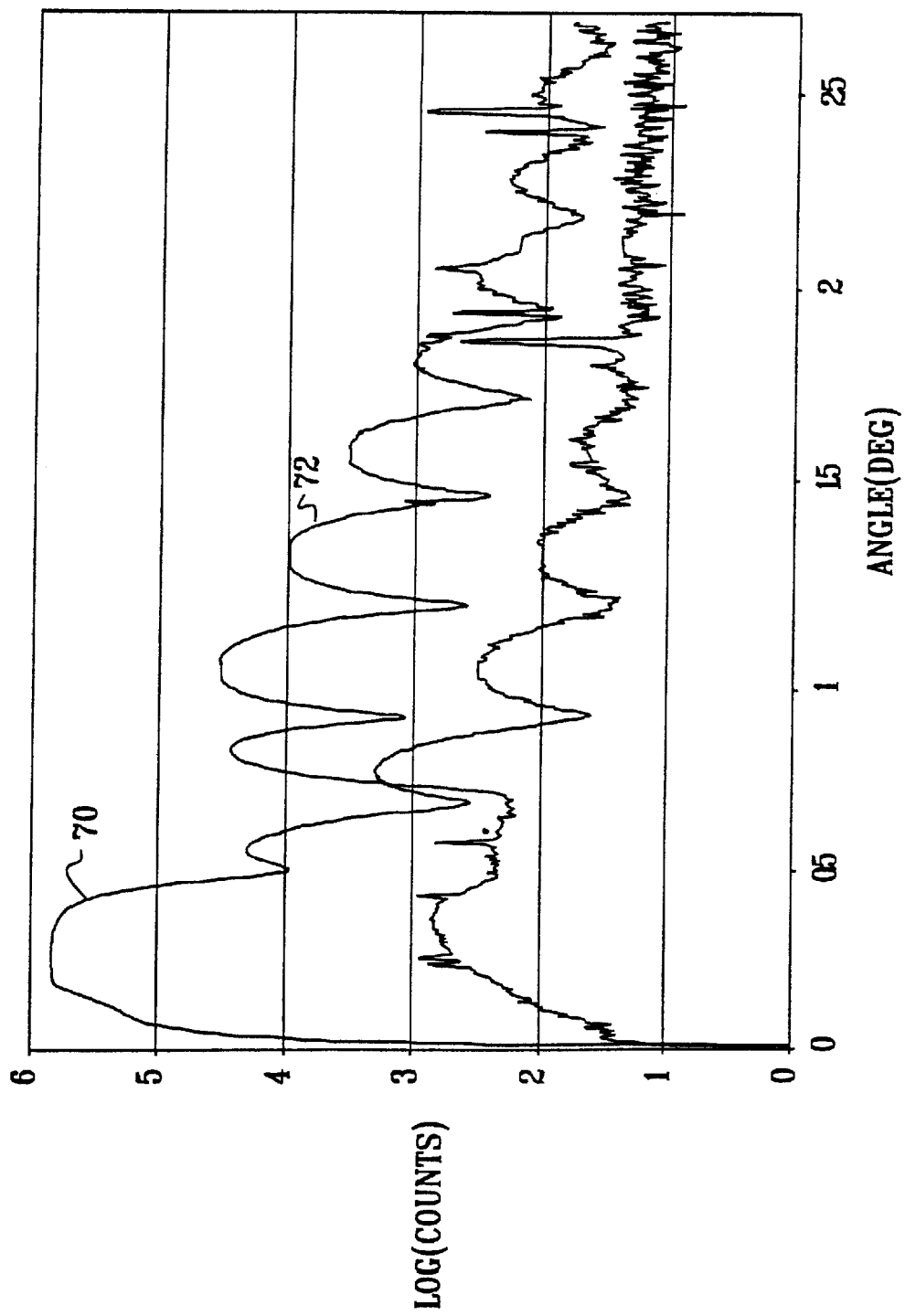
FIG. 6 is a schematic plot of X-ray reflectance signals as a function of reflection angle, under two different sets of detection conditions, in accordance with a preferred embodiment of the present invention.

FIG. 6 is a schematic plot showing reflectometric signals gathered by processor 40, in accordance with a preferred embodiment of the present invention, using dynamic shutter 38 as shown in FIGS. 5A and 5B and the signal processing method of FIG. 4. The plot shows, on a logarithmic scale, the number of counts n(j) accumulated at each pixel as a function of reflection angle. A high-intensity trace 70 is generated in the configuration of FIG. 5A (with or without the use of knife edge 36), using a relatively short exposure. A second, low-intensity trace 72 is generated with shutter 38 positioned to block the low-angle beam, as shown in FIG. 5B, using a long exposure. Trace 70 shows the low-angle fringe structure, while trace 72 shows the high-angle structure. Fringes in an intermediate region (around 1°) can be seen in both traces.

Figure 7:
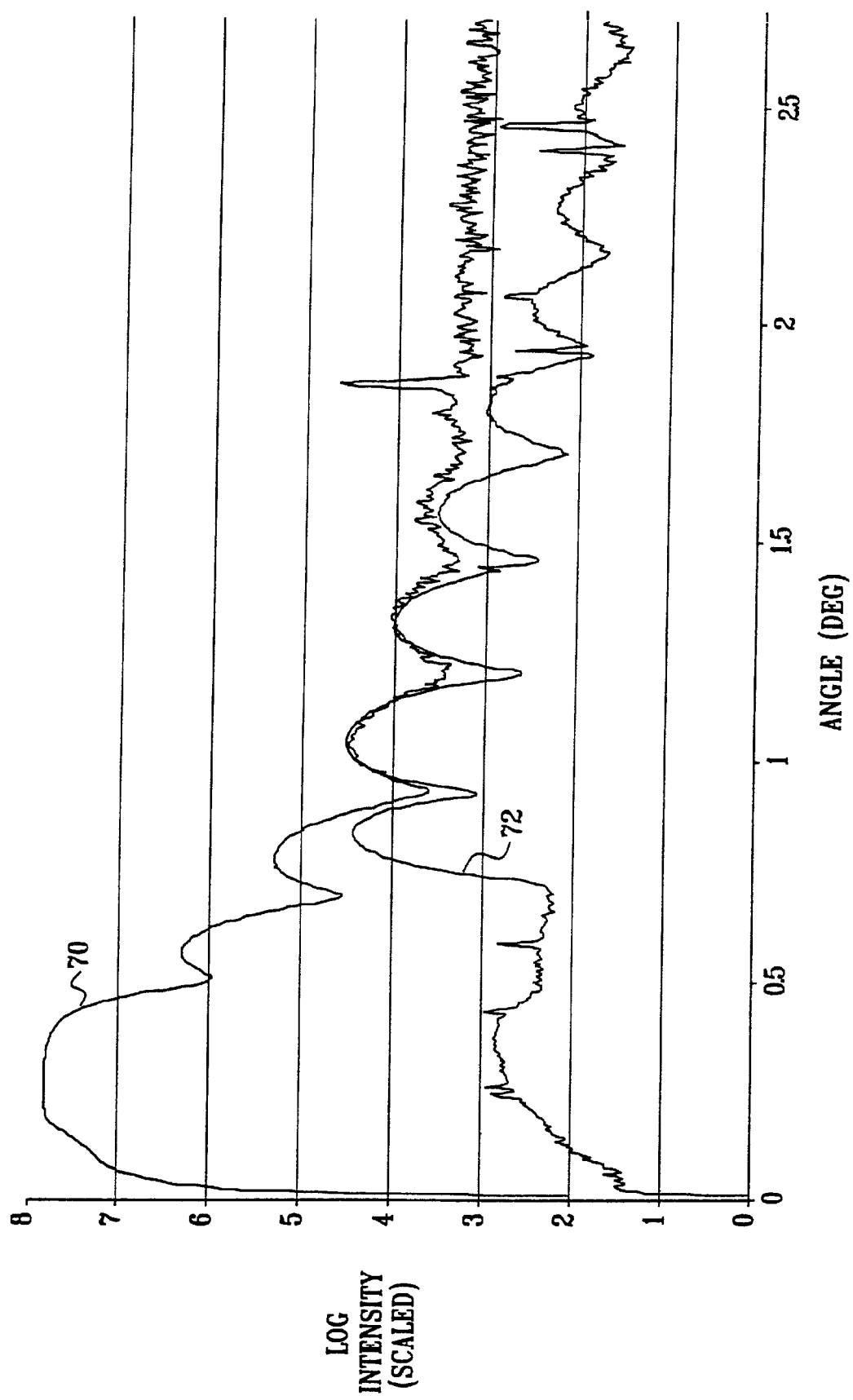
FIG. 7 is a schematic plot illustrating scaling of the signals of FIG. 6, in accordance with a preferred embodiment of the present invention.

FIG. 7 is a schematic plot showing traces 70 and 72 after trace 70 has been scaled to match the amplitude of trace 70 in the intermediate region.

Figure 8:
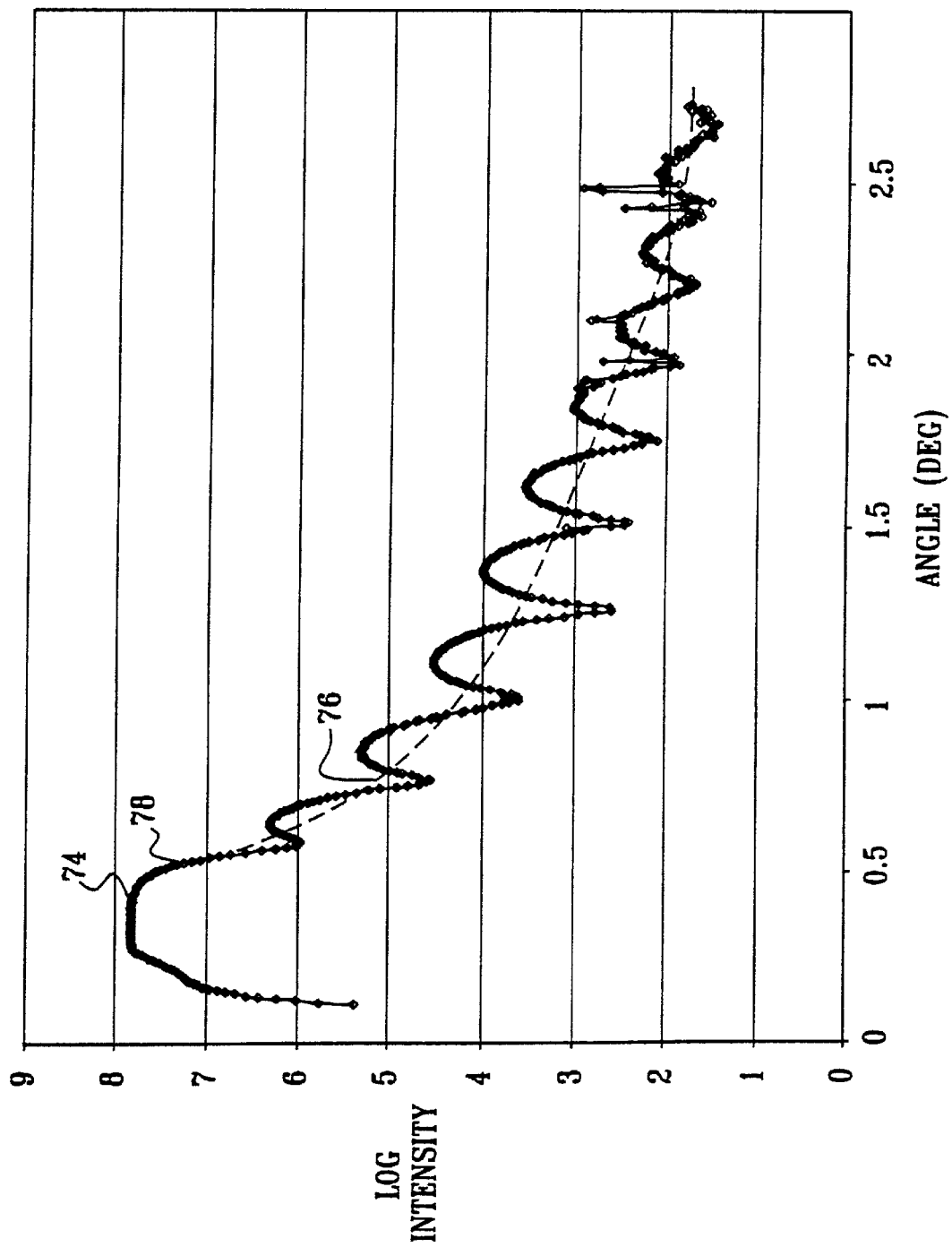
FIG. 8 is a schematic plot illustrating an X-ray reflectance spectrum, formed by combining the signals of FIG. 7, in accordance with a preferred embodiment of the present invention.

FIG. 8 shows a composite trace 74, generated by combining the scaled and superimposed traces 70 and 72 of FIG. 7, in accordance with a preferred embodiment of the present invention. For each pixel, the value in composite trace 74 is a weighted sum of the corresponding values in traces 70 and 72, with weighting factors that vary appropriately as a function of angle. Trace 74 shows a well-defined fringe pattern extending from near 0° out to 2.5°. The high-angle fringes are particularly important in determining properties of inner layers at the surface of sample 22, when a multi-layer thin film structure is to be analyzed. The spikes seen at high angles are experimental artifacts, which are ignored in the analysis described below.

Figure 9:
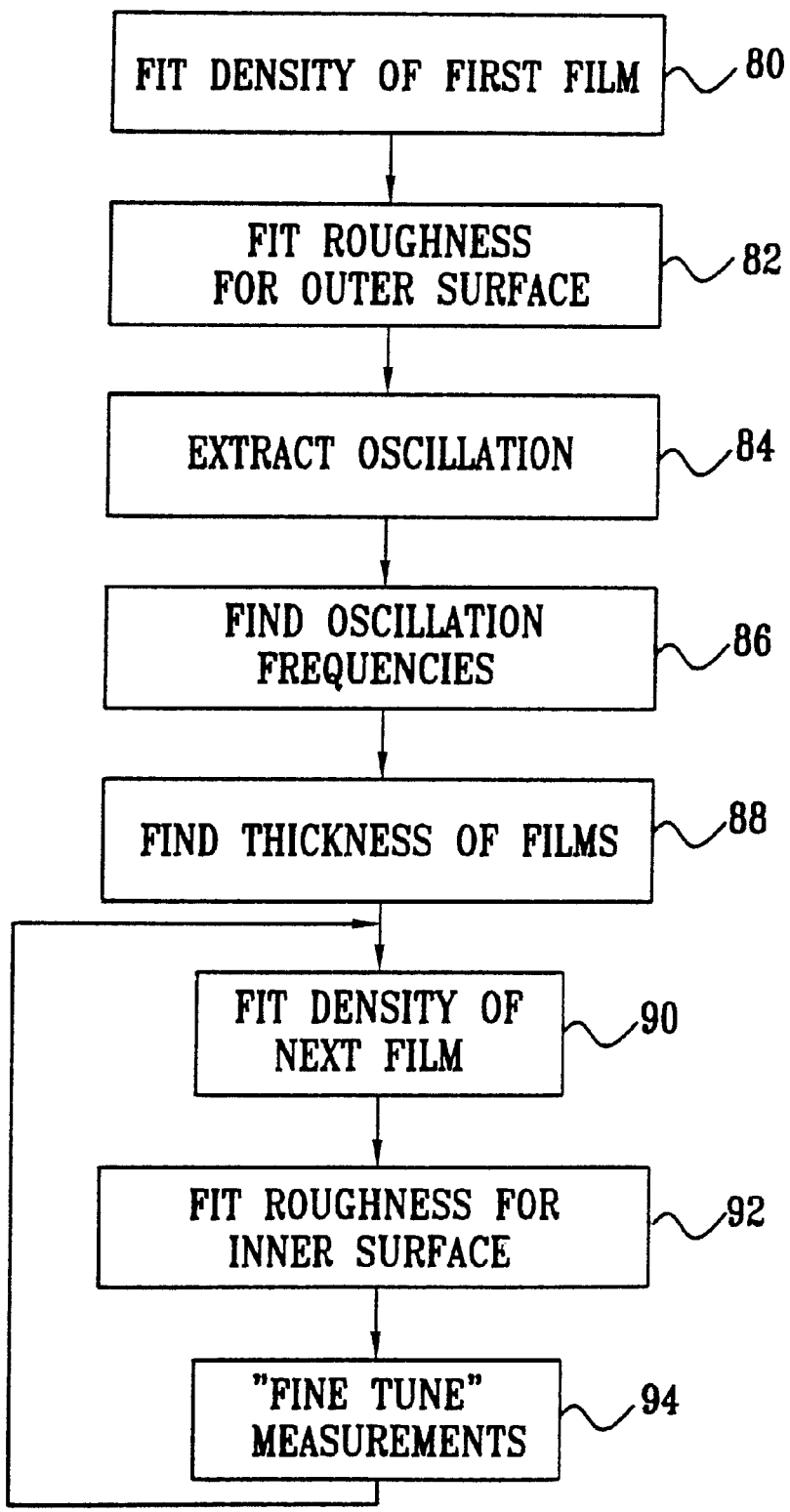
FIG. 9 is a flow chart that schematically illustrates a method for extracting thin film data from an X-ray reflectance spectrum, in accordance with a preferred embodiment of the present invention.

FIG. 9 is a flow chart that schematically illustrates a method for analyzing trace 74 to determine the properties of thin films on sample 22, in accordance with a preferred embodiment of the present invention. The method is based on a physical model of the reflected fringe pattern. According to this model, the angular position of an initial shoulder 78 (FIG. 8) in the fringe pattern is determined mainly by the density of the uppermost layer on the sample. The spatial frequency or frequencies of the fringes are indicative of the thickness of the film layers. The intensity of the higher-order fringes relative to the low-order ones, indicated by a decay curve 76 fitted to trace 74, is determined mainly by the roughness of the outer surface of the sample and, secondarily, of the interfaces between the film layers on the sample.

Based on this model, at a density fitting step 80, an initial, theoretical fringe pattern is fitted to trace 74, by adjusting the density in the model so that the theoretical pattern fits shoulder 78. For the purpose of this step, the film is considered to be infinitely thick, and only the part of the fringe pattern in the immediate vicinity of the shoulder is considered. Next, at a roughness fitting step 82, a parameter in the model corresponding to the roughness of the outer surface of the sample is adjusted so that curve 76 fits the actual, average decay of trace 74 as a function of angle. The fit is performed so that the difference between trace 74 and curve 76, integrated over the entire angular range (or a substantial, selected portion of the range), is close to zero.

The fitted decay curve is subtracted out of trace 74, in order to isolate the oscillatory portion of the reflected signal, at an oscillation extraction step 84. The oscillation frequency or frequencies in the subtracted signal are determined, at a frequency determination step 86, preferably using a Fast Fourier Transform (FFT) analysis of the signal. The frequency spectrum is preferably filtered to eliminate spurious high-frequency components. The filtered spectrum is transformed back to the spatial domain, and a least squares fit is performed to determine the thicknesses of the detected layers on the sample surface, at a thickness measurement step 88. Typically, when the sample has a multi-layer structure, the outer layer will give the strongest frequency component in the spectrum, at a relatively low frequency corresponding to the thickness of this layer. The next frequency component will be at a higher frequency, corresponding to the combined thickness of the outer layer and the next layer below it. The thickness of the next layer is determined by subtracting the outer layer thickness from the combined thickness. Additional layer thicknesses may be determined in like manner if the spectrum is sufficiently well resolved.

Upon completion of step 88, the physical properties of the outer layer on the sample—density, thickness, and outer surface roughness—are all known. Assuming that more than a single frequency was found at step 86, corresponding to a multi-layer structure, trace 74 can be further analyzed to determine the properties of one or more inner layers. At an inner density fitting step 90, the density of the second layer (below the outer layer) is introduced into the theoretical model and is adjusted to produce an optimal fit. A roughness parameter for the surface between the outermost and second layers is adjusted to improve the fit of the model curve to the amplitude of the oscillations in trace 74, at an inner roughness fitting step 92. Thickness parameters, corresponding to possible errors in the thickness of the outermost and second layers, are adjusted at a fine tuning step 94, in order to correct any mismatch between the positions of the fringes and the derived model. To the extent that trace 74 provides sufficient resolution of fine fringe detail, as noted above, steps 90, 92 and 94 may be repeated for further, underlying layers on the sample.

Figure 10:
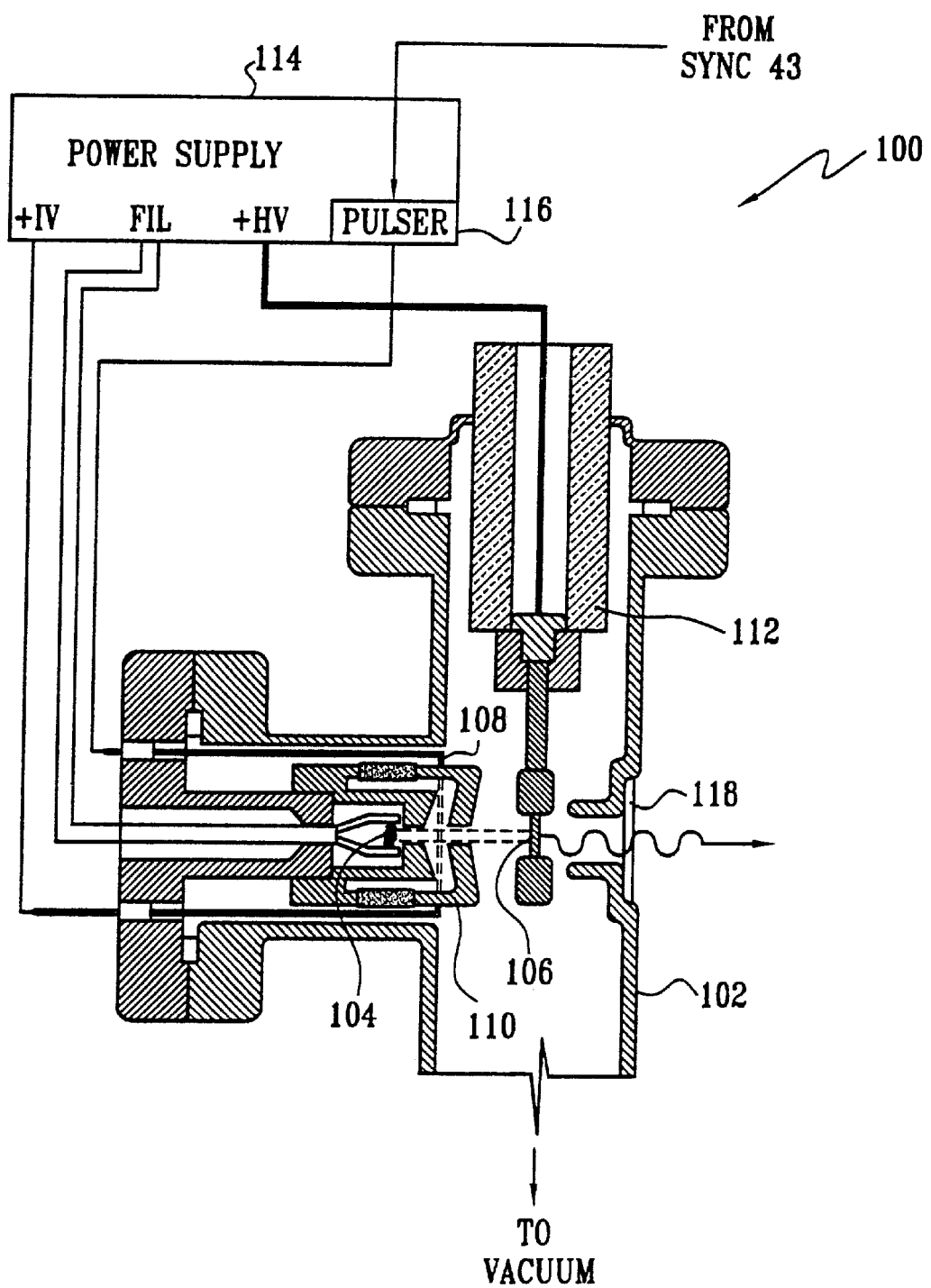
FIG. 10 is a schematic, sectional illustration of a pulsed X-ray tube, useful in implementing a preferred embodiment of the present invention.

FIG. 10 is a schematic, sectional illustration of a pulsed X-ray tube 100, for use in making gated measurements of X-ray reflection from sample 22, in accordance with a preferred embodiment of the present invention. The design of tube 100 is described generally by Jaklevic et al., in "High Rate X-ray Fluorescence Analysis by Pulsed Excitation," *IEEE Transactions on Nuclear Science* NS-19:3 (1972), pp. 392–395, and in "Small X-ray Tubes for Energy Dispersive Analysis Using Semiconductor Spectrometers," *Advances in X-ray Analysis* 15 (1972), pp. 266–275. Both of these articles are incorporated herein by reference. Jaklevic and his associates describe the use of pulsed X-ray excitation to avoid the phenomenon of pulse "pile-up," which occurs in energy-dispersive X-ray fluorescence (ED-XRF) photon counting systems.

Tube 100 comprises an electron source, such as a tungsten filament 104, and an anode 106, which are both contained in an evacuated envelope 102. The anode is held at approximately +40 kV relative to the grounded filament by a power supply 114. A control grid 108 and a screen grid 110 are used to control the passage of electrons from the filament to the anode. The screen grid is held at about +300 V. Between pulses, the control grid is held below a cut-off voltage of −10 V. A pulse generator 116 rapidly pulses the control grid to about +100 V, causing a burst of electrons to pass through the screen grid and strike anode 106. The X-rays thus generated at the anode exit tube 100 through a window 118, and are then focused onto sample 22, as described above.

Referring now to FIGS. 1 and 2, readout circuits 50 of detector assembly 30 are synchronized by synchronization controller 43 to read out the charge from the elements of array 32 just before and just after each pulse of tube 100. Charge that is accumulated in the readout cycle occurring before tube 100 is fired can be due only to background effects, such as thermal noise. This readout is therefore discarded, or is used to establish a baseline noise level for subtraction from the subsequent signal. The charge accumulated in the cycle after the tube is pulsed represents the signal, due to reflection of X-ray photons from the sample, with a substantial enhancement of signal/noise ratio.

To appreciate the enhancement of signal/noise ratio by the present embodiment, assume the average total noise level is N counts/sec, and assembly 30 is read out at a constant rate of M frames/sec. Under these conditions, circuits 50 will read out on average N/M noise counts per frame. When X-ray source 26 operates continuously at an average output power level P, as in systems known in the art, the reflected signal sensed by array 32 in each frame is proportional to P/M, so that the signal/noise ratio of system 20 in each frame is proportional to (P/M)/(N/M)=P/N. On the other hand, when tube 100 is pulsed once per second, for example, while maintaining the same average output power level P, the entire reflected signal due to P is gathered in a single frame, while the noise level remains constant. Thus, the signal/noise ratio is now P/(N/M), giving an M-fold enhancement over conventional, continuous operation (neglecting possible enhancement of the signal/noise ratio in the continuous case by signal averaging, which can improve the ratio by $\sqrt{M}$).

This large enhancement of signal/noise ratio in pulsed operation is based on the assumption that there are no saturation effects and thermal noise is the dominant noise source. The optimal pulse rate and other operating parameters for tube 100 will depend in each case on the characteristics of the tube, sample and detector assembly. It is clear, however, that under appropriate operating conditions, the use of pulsed tube 100 in system 20 can provide a substantially better signal/noise ratio than can a continuous-wave (CW) tube running at the same average power level.

Although the features of system 20 have been described here in combination, it will be appreciated that individual ones or subgroups of these features can also be used independently of the other features. Furthermore, although these features are described in the context of X-ray reflectometry, at least some of them are also applicable in other fields of analysis, such as diffractometry, using X-rays and other radiation bands.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Reflectometry apparatus, comprising:

a pulsed X-ray source, adapted to irradiate a sample with a sequence of pulses of radiation over a range of angles relative to a surface of the sample;

an array of detector elements, positioned to receive the radiation reflected from the sample over the range of angles and to generate a signal indicative of respective charges accumulated by the detector elements due to photons of the radiation that are incident on the elements; and timing circuitry, coupled to the array so as to cause the charges to be cleared from the detector elements immediately before each of the pulses in the sequence, and to cause the signal from the elements to be sampled shortly after each of the pulses.

2. Apparatus according to claim 1, wherein the sample comprises one or more thin film layers, and wherein the reflected radiation is characterized by an oscillatory variation of intensity as a function of the angles due to the thin film layers, and wherein the array of detector elements is adapted to detect the oscillatory variation.

3. Apparatus according to claim 2, and comprising a processor, which is coupled to receive the signal from the array of detector elements and to analyze the oscillatory variation to determine one or more properties of the one or more thin film layers.

4. Apparatus according to claim 3, wherein the processor is adapted to estimate, responsive to the respective charges, a number of the photons that was incident on each of the elements.

5. Apparatus according to claim 1, wherein the detector elements are characterized by a background current, which causes a noise charge to be accumulated by the detector elements irrespective of the radiation, and wherein by causing the charges to be cleared from the detector elements, the timing circuitry is operative to reduce the noise charge in the signal sampled from the elements shortly after each of the pulses.

6. Apparatus according to claim 5, wherein the array of detector elements comprises a charge coupled device (CCD).

7. Apparatus according to claim 1, wherein the timing circuitry is coupled to synchronize clearing of the charges from the detector elements and sampling of the signal therefrom with the pulses from the X-ray source.

8. A method for reflectometry, comprising:

positioning an array of detector elements to receive radiation reflected from a sample and to generate, responsive to the radiation, a signal indicative of respective charges accumulated by the detector elements due to photons of the radiation that are incident on the elements;

irradiating a sample with a sequence of pulses of the radiation over a range of angles relative to a surface of the sample;

clearing the charges from the detector elements immediately before each of the pulses in the sequence; and sampling the signal from the elements shortly after each of the pulses so as to determine a pattern of the reflected radiation over the range of angles.

9. A method according to claim 8, wherein the sample comprises one or more thin film layers, and wherein the reflected radiation is characterized by an oscillatory variation of intensity as a function of the angles due to the thin film layers, and wherein sampling the signal comprises detecting the oscillatory variation.

10. A method according to claim 9, and comprising analyzing the oscillatory variation in the signal so as to determine one or more properties of the one or more thin film layers.

11. A method according to claim 10, wherein detecting the oscillatory variation comprises determining, responsive to the respective charges, a number of the photons that was incident on each of the elements.

12. A method according to claim 8, wherein the detector elements are characterized by a background current, which causes a noise charge to be accumulated by the detector elements irrespective of the radiation, and wherein clearing the charges comprises reducing the noise charge in the signal sampled from the elements shortly after each of the pulses.

13. A method according to claim 12, wherein the array of detector elements comprises a charge coupled device (CCD).

14. A method according to claim 8, wherein clearing the charges and sampling the signal comprise synchronizing the clearing and the sampling with the pulses from the X-ray source.

* * * * *